United States Patent [19]

Farber

[11] 4,020,068
[45] Apr. 26, 1977

[54] CHROMOGENIC FUROQUINOXALINES

[75] Inventor: Sheldon Farber, Appleton, Wis.

[73] Assignee: NCR Corporation, Dayton, Ohio

[22] Filed: Feb. 28, 1975

[21] Appl. No.: 554,257

Related U.S. Application Data

[63] Continuation-in-part of Ser. No. 468,112, May 8, 1974, abandoned.

[52] U.S. Cl. .................. 260/250 Q; 282/27.5
[51] Int. Cl.² .............................. C07D 491/04
[58] Field of Search ........................ 260/250 Q

[56] References Cited
OTHER PUBLICATIONS
Dahn et al., Chem. Abs. 62, 7756e (1964).

*Primary Examiner*—Donald G. Daus
*Assistant Examiner*—Mark L. Berch
*Attorney, Agent, or Firm*—E. Frank McKinney

[57] ABSTRACT

A chromogenic compound of normally colorless form is disclosed having the following structural formula:

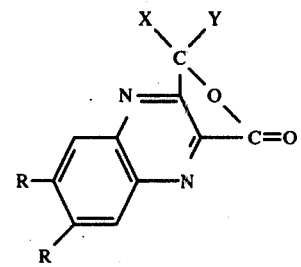

wherein X and Y can be

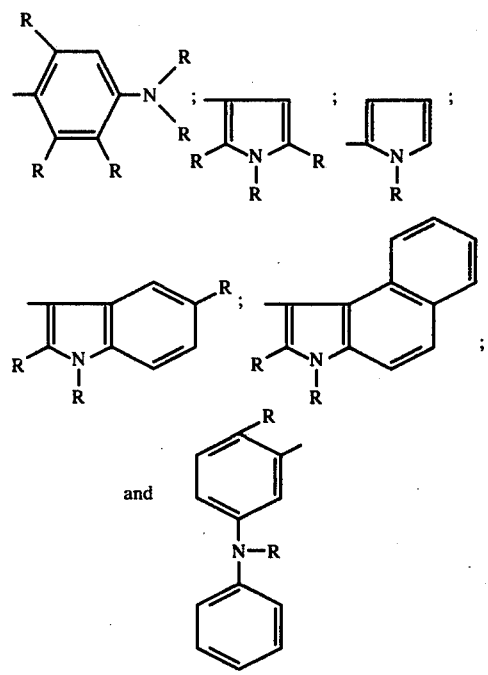

and R can be hydrogen, chlorine, nitro, phenyl, benzyl, alkyl, alkoxy, and dialkylamino. The compound is eligible for use in pressure-sensitive record material and mark-forming manifold systems.

6 Claims, 1 Drawing Figure

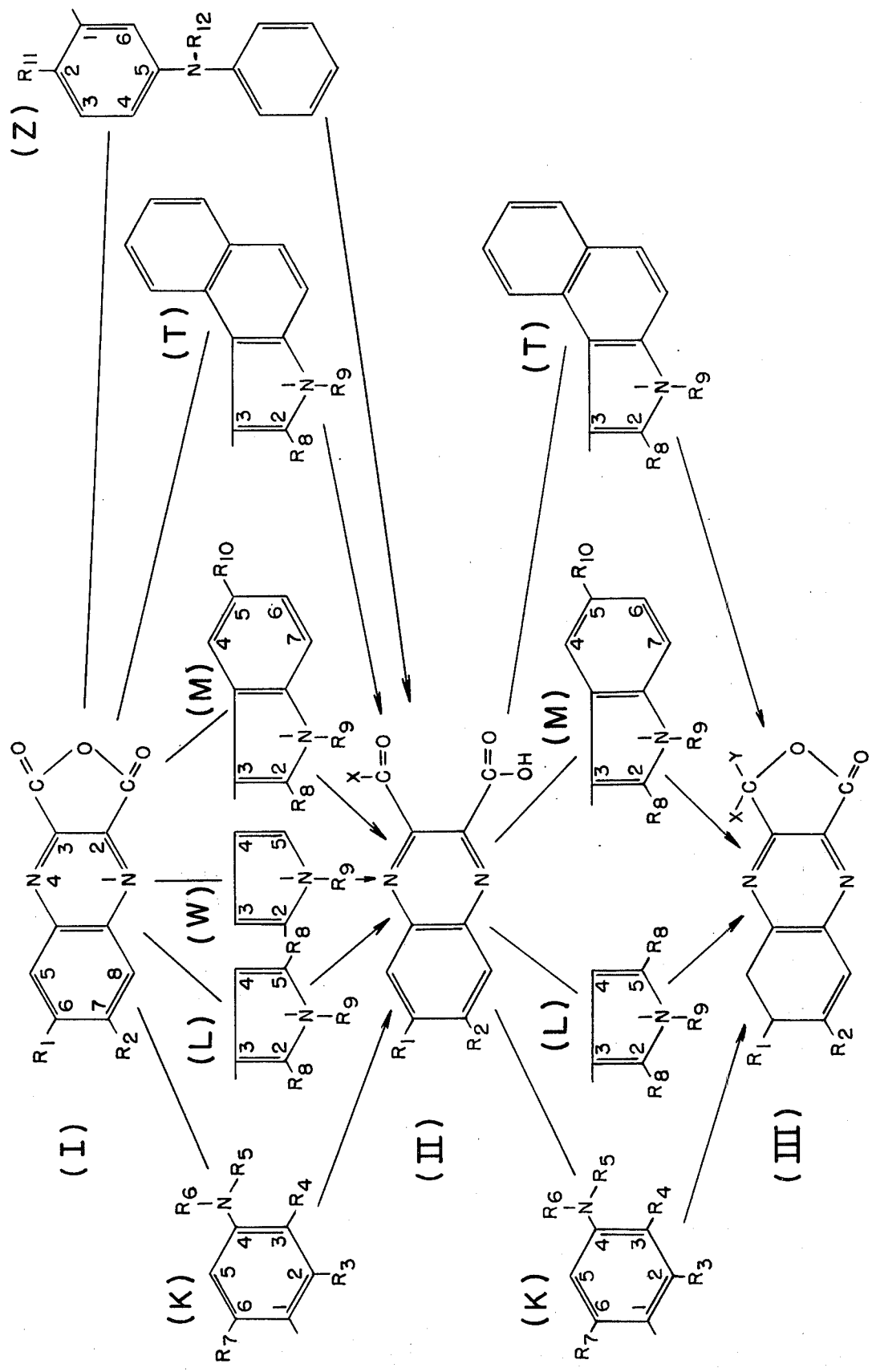

CHROMOGENIC FUROQUINOXALINES

Under 35 U.S.C. 120, the benefit of the filing date of U.S. patent application Ser. No. 468,112, filed May 8, 1974, now abandoned of which case this is a C.I.P. is claimed herein.

BACKGROUND OF THE INVENTION

1. Field of the Invention

This invention pertains to colorable chromogenic compounds eligible for use in pressure-sensitive record material. Pressure-sensitive mark-forming record systems, single sheet and manifold, are improved by use of these compounds.

More specifically, this invention relates to chromogenic compounds having a quinoxaline moiety which compounds have the form of substantially colorless or slightly colored solids, or which approach being colorless when in liquid solution; but which may be converted to dark-colored forms upon reactive contact with acidic material. As used in mark-forming systems, marking in desired areas on support webs or sheets may be accomplished by effecting localized reactive contact between the chromogenic material and the acidic material on or in such web or sheet, such material being brought thereto by transfer, or originally there in situ, the desired reactive contact forming dark-colored materials in the intended image-marking areas.

2. Description of the Prior Art

Several phthalide chromogenic compounds have been disclosed. For example, U.S. Pat. No. 3,491,111, issued Jan. 20, 1970, discloses indole- and carbazol-substituted phthalides.

Pyridine- and pyrazine-containing chromogenic compounds have also been disclosed. For example, U.S. Pat. No. 3,775,424, issued Nov. 27, 1973, discloses furo[3-4b]-pyridine-7(5H)-ones, among others.

U.S. Pat. No. 3,672,935, issued June 27, 1972, discloses use of colorless chromogenic compounds in pressure-sensitive record material.

SUMMARY OF THE INVENTION

Colorable chromogenic compounds having a quinoxaline moiety have been discovered which compounds are initially colorless but produce dark-colored products on reaction with certain acid materials. The quinoxaline chromogenic compounds exhibit high color intensity and resistance to fade when exposed to light. It is an object of this invention to provide such quinoxaline compounds and methods for making them.

An important use for the quinoxaline compounds of this invention resides in their incorporation into pressure-sensitive record systems as a colorable reactant for development of color on application of a mark-forming force. Hence, it is an object of this invention to provide substances having chromogenic properties, which substances can be incorporated in a web or coated onto the surface of a web to provide a record sheet or a manifolding unit, and which are useful in carrying out methods of marking involving reactive contact with a color-activating material to develop dark-colored materials in areas where marking is desired.

It is an object of this invention to provide modified compounds, based upon the afore-mentioned quinoxaline compounds, which are substantially colorless, or slightly colored, offering a variety of chromogenic characteristics, and developing dark-colored substances upon contact with color-activating materials.

BRIEF DESCRIPTION OF THE DRAWING

The quinoxaline compounds of this invention include a variety of several moieties with the quinoxaline moiety being necessarily common to all. In order to more completely and more distinctly disclose the variety of moiety combinations which forms a part of this invention, a drawing is included which is a schematic representation of the combination, by structural formula.

The drawing presents a step-by-step structural development of the quinoxaline compounds of this invention, as they can be prepared. A quinoxaline dicarboxylic anhydride (I) is combined with a substrate reactant to yield a quinoxaline keto acid (II) which is, in turn, combined with a substrate reactant to yield the quinoxaline chromogenic compound (III) of this invention.

The dicarboxylic anhydride (I) includes $R_1$ and $R_2$ at the 6 and 7 quinoxaline positions, respectively. $R_1$ and $R_2$ represent hydrogen, chlorine, nitro, alkyl, alkoxy, and dialkylamino, wherein the alkyl and the alkoxy represent methyl and methoxy, ethyl and ethoxy, propyl and propoxy (including isopropyl and isopropoxy), butyl and butoxy (including isobutyl and isobutoxy and tert-butyl and tert-butoxy), pentyl and pentoxy (including five-carbon isomers), hexyl and hexoxy (including six-carbon isomers) and the like having less than seven carbon atoms.

The substrate reactant, 4-aminophenyl (K) includes $R_3$ at the 2 phenyl position, $R_4$ at the 3 phenyl position, $R_5$ and $R_6$ on the amino at the 4 position, and $R_7$ at the 6 position. $R_3$, $R_4$, and $R_7$ represent hydrogen, chlorine, nitro, alkyl, alkoxy, and dialkylamino wherein the alkyl and the alkoxy represent less than seven carbon atoms, as described above. $R_5$ and $R_6$ represent hydrogen, phenyl, benzyl and alkyl wherein the alkyl represents less than seven carbon atoms, as described above and, additionally, if one of $R_5$ and $R_6$ is phenyl or benzyl, the other must be hydrogen or methyl.

The substrate reactant 3-pyrryl (L) includes $R_8$ at the 2 and the 5 pyrrole positions and $R_9$ at the 1 pyrrole position. The substrate reactant, 3-indolyl (M) includes $R_8$ and $R_9$ at the 2 and the 1 indole positions, respectively, and $R_{10}$ at the 5 indole position. The substrate reactant, 3-benzoindolyl (T), includes $R_8$ and $R_9$ at the 2 and the 1 benzoindole positions, respectively. The substrate reactant, 2-pyrryl (W) includes $R_9$ at the 1 pyrrole position. The substrate reactant, (2-alkoxy-5-anilino)phenyl (Z) includes $R_{11}$ at the 2 phenyl position and $R_{12}$ at the anilino nitrogen. $R_8$ represents hydrogen, alkyl, alkoxy, and phenyl wherein the alkyl and the alkoxy represent less than seven carbon atoms, as described above. $R_9$ represents hydrogen, alkyl, and phenyl wherein the alkyl represents less than seven carbon atoms, as described above. $R_{10}$ represents hydrogen, alkyl, and alkoxy wherein the alkyl represents less than seven carbon atoms, as described above. $R_{11}$ represents alkoxy with less than seven carbon atoms, as described above. $R_{12}$ represents hydrogen, methyl, and ethyl.

The compound (III) is the chromogenic compound of this invention;—X representing any of substrate reactants (K), (L), (M), (T), (W), and (Z); and Y representing any of substrate reactants (K), (L), (M) and (T).

DETAILED DESCRIPTION OF THE INVENTION

Any detailed description of the invention must, for the sake of completeness, include a statement of the use to which the quinoxaline compounds are most preferredly put. At the present time, the chromogenic quinoxaline compounds of this invention enjoy extensive eligibility for use in pressure-sensitive mark-forming systems.

Pressure-sensitive mark-forming systems provide a marking system of disposing on and/or within sheet support material unreacted mark-forming components and a liquid solvent in which each of the mark-forming components is soluble, said liquid solvent being present in such form that it is maintained isolated by a pressure-rupturable barrier, from at least one of the mark-forming components until application of pressure causes a breach of the barrier in the area delineated by the pressure pattern. The mark-forming components are thereby brought into reactive contact, producing a distinctive mark.

The method of marking of this invention, i.e., by developing a dark-colored material from substantially colorless or slightly colored chromogenic compounds, comprises providing a chromogenic compound selected from among the above-mentioned compounds and bringing such chromogenic compound into reactive contact, in areas where marking is desired, with an acidic color-activating substance to produce a dark-colored resonant form of the chromogenic compound.

The acidic materials employed in this invention can be any compound within the definition of a Lewis acid, i.e., an electron acceptor. Preferably, acidic organic polymers such as phenolic polymers are employed as the acidic material. It is noted that the polymeric mark-forming components should have a common solubility with the chromogenic compound in at least one liquid solvent when the acid-reacting material is a phenolic or other organic acidic polymer. It is also noted that in a single system several chromogenic compounds can be used with the same or different polymeric materials. Several polymeric materials can be reactively contacted with a single chromogenic compound or with a mixture of chromogenic compounds.

The acidic polymeric material useful in this invention includes phenol polymers, phenol acetylene polymers, alkyl-phenol-acetylene polymers, maleic acid-rosin resins, partially or wholly hydrolyzed styrene-maleic anhydride copolymers and ethylene-maleic anhydride copolymers, carboxy polymethylene and wholly or partially hyrolyzed vinyl methyl ether maleic anhydride copolymers and mixtures thereof.

When the acidic material is one of the aforementioned organic polymers, the liquid solvent chosen must be capable of dissolving the mark-forming components. The solvent can be volatile or non-volatile, and a single or multiple component solvent may be used which is wholly or partially volatile. Examples of volatile solvents useful in the aforedescribed basic chromogen-acidic polymer are toluene, petroleum distillate, perchloroethylene, and xylene. Examples of non-volatile solvents are high-boiling point petroleum fractions, dioctyl adipate, biphenyls, diphenyl alkanes, and the like.

Generally, the solvent chosen should be capable of dissolving at least 0.3 percent, by weight, of the chromogenic compounds and at least about 3–5 percent, by weight, of the polymeric material. A further criterion of the solvent is that it must not interfere with the mark-forming reaction.

The support member on which the components of the system are disposed may comprise a single or dual sheet assembly. In the case where all components are disposed on a single sheet, the record material is referred to as a "self-contained" system. Where there must be a migration of the solvent, with or without mark-forming component, from one sheet to another, the record material is referred to as a "transfer" system. (Such a system can also be referred to as a "two-fold" system, in that at least two sheets are required and each sheet includes a component, or components, essential to the mark-forming reaction.) Where a copious amount of the colored reaction product in liquid form is produced on a surface of one sheet, it can produce a mark by transfer to a second sheet as a colored mark.

The polymeric material can be dissolved in ink composition vehicles to form a printing "ink" of colorless character and, thus, can be used to spot-print a proposed record sheet unit sensitized for recording in a reaction-produced color in those areas by application of a solution of the chromogenic material. In the case of phenolic polymer, a printing ink can be made of up to 75%, by weight, of the phenolic polymeric material in a petroleum solvent to a viscosity suitable for printing purposes.

In the mark-forming system herein, the acidic mark-forming component(s) reacts with the chromogenic material(s) to effect distinctive color formation or color change. In a multi-sheet system in which an acid organic polymer is employed, it is desirable to include other materials to supplement the reactants. For example, kaolin can be added to improve the transfer of the liquid and/or the dissolved materials between the sheets. In addition, other materials such as bentonite, attapulgite, talc, feldspar, halloysite, magnesium trisilicate, silica gel, propyllite, zinc sulfide, calcium sulfate, calcium citrate, calcium phosphate, calcium fluoride, barium sulfate and tannic acid can be included. It should be noted that mineral materials such as kaolin, attapulgite, silica gel, silton clay, and the like can, also, be used alone or in combination with other materials as an acidic material coreactant.

Various methods known to the prior art and disclosed in the aforementioned U.S. Pat. No. 3,672,935 can be employed in coating compositions of the mark-forming materials into their supporting sheets. An example of the compositions which can be coated onto the surface of an underlying sheet of a two-sheet system to react with the chromogenic material on the underside of any overlying sheet is as follows:

| Coating Composition | Percent by Weight |
|---|---|
| Phenolic polymer mixture | 17 |
| Paper coating kaolin (white) | 57 |
| Calcium carbonate | 12 |
| Styrene butadiene latex | 4 |
| Ethylated starch | 8 |
| Gum arabic | 2 |
| | 100 |

This invention is further illustrated by the following examples. The reactants and the proportions and other specific conditions are represented as being typical and should not be construed to limit the invention.

DESCRIPTION OF PREFERRED EMBODIMENTS

Preparation A

Preparation of 2-(2-methyl-4-diethylaminobenzoyl)-3-quinoxalinic acid.

In this preparation, N,N-diethyl-m-toluidine (moiety, K, where $R_3=CH_3$, $R_4=H$, $R_5=R_6=C_2H_5$ and $R_7=H$) is combined with 2,3-quinoxalinic anhydride (I, wherein $R_1=R_2=H$) to yield the title compound. This preparation can also be completed using 6,7-di-(diethylamino)-2,3-quinoxalinic anhydride (I, wherein $R_1=R_2=N(C_2H_5)_2$) and 6,7-di-isopropyl-2,3-quinoxalinic anhydride (I, wherein $R_1=R_2=C_3H_7$). One-tenth mole of the toluidine and 0.1 mole of anhydrous aluminum chloride are added to 50 milliliters of, ice-cooled, methylene chloride. To that system, is added 0.02 mole of the quinoxalinic anhydride, and the system is stirred overnight to permit completion of the reaction. The system is steam-distilled and the solid residue is separated by filtration. The solid residue is dissolved in ammonia and reprecipitated with dilute hydrochloric acid at about pH 2.

EXAMPLE 1

Combining a quinoxalinic acid from Preparation A, above, with a dialkyltoluidine, results in a compound of this invention. This example will be given with details of the reaction conditions and will be followed by a table of exemplary compounds. A mixture of 0.9 grams of the title compound from Preparation A, 0.4 grams of N,N-diethyl-m-toluidine (moiety, K, wherein $R_3=CH_3$, $R_4=H$, $R_5=R_6=C_2H_5$ and $R_7=H$), and 5 milliliters of acetic anhydride is refluxed for five minutes and poured into ice and ammonia. The system is extracted twice with toluene, dried in the toluene using sodium sulfate, and the toluene is evaporated. The residue is dissolved in chloroform and chromatographed on alumina using chloroform as the eluting solvent. Solvent from the eluted fraction is evaporated and the material is recrystallized three times from toluene-petroleum ether and once from toluene. The resulting product is 1,1-bis-(3-methyl-4-diethylaminophenyl)-1-[H]-3-[H]-furo[3,4-b]quinoxalin-3-one, exhibits a melting point of 181°–6° C., and a chloroform solution of the product imparts a brilliant green color to paper coated with a phenolic resin or silton clay or a combination of the two. This example can also be conducted using 1-diethylamino-3-ethylbenzene (K, wherein $R_3=C_2H_5$, $R_4=H$, $R_5=R_6=C_2H_5$, $R_7=H$) and 1-dibutylamino-3-diethylaminobenzene (K, wherein $R_3=N(C_4H_9)_2$, $R_4=H$, $R_5=R_6=C_2H_5$, $R_7=H$):

TABLE I

| Ex. No. | Moiety | | | | Substituents | | | | | Color |
|---|---|---|---|---|---|---|---|---|---|---|
| 2 | (K) | $R_3=$ | H | $R_4=$ | H | | $R_5=R_6=$ | $C_2H_5$ | $R_7=$ H | Green |
| | | | H | | i-$C_6H_{13}$ | | | $C_2H_5$ | H | |
| | | | H | | $OC_3H_7$ | | | $C_2H_5$ | H | |
| | | | H | | $NO_2$ | | | t-$C_4H_9$ | H | |
| | | | H | | Cl | | | $C_2H_5$ | H | |
| 3 | (K) | $R_3=$ | $OC_2H_5$ | $R_4=$ 32 | H | | $R_5=R_6=$ | $C_2H_5$ | $R_7=$ H | Blue |
| | | | H | | H | | | $C_2H_5$ | $OC_2H_5$ | |
| | | | $OC_6H_{13}$ | | H | | | $C_2H_5$ | H | |
| | | | H | | H | | | $C_2H_5$ | $NO_2$ | |
| 4 | (K) | $R_3=$ | $CH_3$ | $R_4=$ | H | $R_5=$ $CH_3$ | $R_6=$ | benzyl | $R_7=$ H | Green |
| | | | H | | H | H | | phenyl | H | Purple |
| 5 | (L) | $R_4=$ | $CH_3$ | $R_8=$ | $CH_3$ | | | | | Blue |
| | | | H | | H | | | | | Blue |
| 6 | (M) | $R_4=$ | $CH_3$ | $R_8=$ | $C_2H_5$ | $R_{10}=$ H | | | | Blue-Green |
| | | | $CH_3$ | | H | $CH_3$ | | | | Blue |
| | | | $CH_3$ | | H | $OCH_3$ | | | | Blue |
| | | | i-$C_3H_7$ | | $CH_3$ | H | | | | |
| 7 | (T) | $R_8=$ | $CH_3$ | $R_9=$ | $C_2H_5$ | | | | | Blue |
| | | | H | | i-$C_6H_{13}$ | | | | | |
| | | | H | | phenyl | | | | | |
| | | | $OC_4H_9$ | | H | | | | | |
| 8 | (W) | $R_9=$ | $CH_3$ | | | | | | | Blue |
| | | | phenyl | | | | | | | Blue |
| 9 | (Z) | $R_{11}=$ | $OCH_3$ | $R_{12}=$ | H | | | | | Green |
| | | | $OC_6H_{13}$ | | H | | | | | |

Preparation B

Preparation of 2-(2-ethoxy-4-diethylaminobenzoyl)-3-quinoxalinic acid.

In this preparation, N,N-diethyl-m-phenetidine (K, wherein $R_3=OC_2H_5$, $R_4=H$, $R_5=R_6=C_2H_5$, $R_7=H$) is combined with 2,3-quinoxalinic anhydride (I, wherein $R_1=R_2=H$) to yield the title compound. This preparation can also be completed using 6-dibutylamino-2,3-quinoxalinic anhydride (I, wherein $R_1=N(C_4H_9)_2$, $R_2=H$) and 6-hexoxy-2,3-quinoxalinic anhydride (I, wherein $R_1=OC_6H_{13}$, $R_2=H$). One-tenth mole of the phenetidine and 0.1 mole of anhydrous aluminum chloride are added to 100 milliliters of tetrachloroethane at about 5 degrees centigrade. About 0.05 mole of the 2,3-quinoxalinic anhydride is slowly added to that system while maintaining the temperature. The system is permitted to warm to about 15 degrees centigrade, is stirred for about 1 hour and is then poured over ice and dilute hydrochloric acid solution. The pH of the system is adjusted to about 2 and about 10.5 grams of a crystallized oil is separated. The separated material is recrystallized several times from ethyl alcohol water and resulting product exhibits a melting point of 175°–176° C.

In an elemental analysis, the calculated elemental amounts for the title compound, by weight percent, are; C, 67.16; N, 10.68; H, 5.89. The elemental amounts found in the above preparation were: C, 67.12; N, 10.59; H, 5.91.

EXAMPLE 10

Combining a quinoxalinic acid from Preparation B, above, with an indole, results in a compound of this invention. This example will be given with details of the reaction conditions and will be followed by a table of exemplary compounds. A mixture of 2.0 grams of the title compound from Preparation B, 1.14 grams of 1-isopentyl-2-methylindole (M, wherein $R_8=CH_3$, $R_9=C_5H_{11}$, $R_{10}=H$), and 10 milliliters of acetic anhydride is stirred at about 50 degrees centigrade for about 1 hour and is then poured into ice and ammonia. The system is extracted twice with toluene, dried in the toluene using sodium sulfate, and the toluene is evaporated. The residue is repeatedly recrystallized from toluene and exhibits a melting point of 179°–180° C. The resulting product is 1-(1-isopentyl-2-methylindol-3-yl)-1-(2-ethoxy-4-diethylaminophenyl)-1-[H]-3-[H]-furo[3,4-b]-quinoxalin-3-one and a solution of the product imparts a deep blue color to paper coated with a phenolic resin or silton clay or a combination of the two.

In an elemental analysis, the calculated elemental amounts for the above product, by weight percent, are: C, 74.97; N, 9.71; H, 6.99. The elemental amounts found in the above preparation were: C, 75.00; N, 9.78; H, 7.05.

liters of tetrachloroethane and stirred for about 10 minutes. To that system, initially cooled to about 5 degrees centigrade, is added 0.06 mole of the 2,3-quinoxalinic anhydride, and the system is stirred for 1-2 hours at about 25 degrees centigrade. The resulting mixture is poured over about 200 grams of ice in 20 milliliters of concentrated hydrochloric acid and then is steam distilled. The resulting precipitation is repeatedly recrystallized from acetonitrile and exhibits a melting point of 193.5°–194° centigrade.

In an elemental analysis, the calculated elemental amounts for the title compound, by weight percent, are: C, 62.58; N, 10.95; H, 4.73; Cl, 9.24. The elemental amounts found in the above preparation were: C, 62.61; N, 11.00; H, 4.65; Cl, 9.25.

EXAMPLE 18

Combining a quinoxalinic acid from Preparation C, above, with an aniline, results in a compound of this invention. This example will be given with details of eligible reaction conditions and will be followed by a table of exemplary compounds. A mixture of 3.86 grams of the title compound from Preparation C, 2.1 grams of m-chloro-N,N-diethylaniline (K, wherein $R_3=Cl$, $R_4=H$, $R_5=R_6=C_2H_5$ and $R_7=H$), and 25 milliliters of acetic anhydride is heated in a sealed tube for about 16 hours at a temperature of about 199 degrees

TABLE II

| Ex. No. | Moiety | | | Substituents | | | | | Color |
|---|---|---|---|---|---|---|---|---|---|
| 11 | (K) | $R_3=$ | H | $R_4=$ | H | $R_5=R_6=$ | $C_2H_5$ | $R_7=$ H | Green-Blue |
| | | | H | | $C_2H_5$ | | $C_2H_5$ | H | |
| | | | H | | $C_3H_7$ | | $C_2H_5$ | H | |
| | | | H | | $N(C_2H_5)_2$ | | $C_2H_5$ | H | Green |
| | | | H | | $N(C_4H_9)_2$ | | $C_2H_5$ | H | |
| 12 | (K) | $R_3=$ | $CH_3$ | $R_4=$ | H | $R_5=R_6=$ | $C_2H_5$ | $R_7=$ H | Green |
| | | | $CH_3$ | | H | | $C_2H_5$ | $CH_3$ | Green |
| | | | $CH_3$ | | H | | $C_2H_5$ | Cl | |
| | | | $OC_2H_5$ | | H | | $C_2H_5$ | H | Green-Blue |
| | | | $NO_2$ | | H | | $C_2H_5$ | H | Green |
| 13 | (L) | $R_8=$ | $CH_3$ | $R_9=$ | $CH_3$ | | | | Purple |
| | | | $CH_3$ | | phenyl | | | | |
| | | | $CH_3$ | | $C_4H_9$ | | | | |
| 14 | (M) | $R_8=$ | H | $R_9=$ | phenyl | $R_{10}=$ | H | | |
| | | $R_8=$ | $CH_3$ | | $C_2H_5$ | | H | | Blue |
| | | | $CH_3$ | | H | | $CH_3$ | | Blue |
| | | | $CH_3$ | | H | | $OCH_3$ | | Blue |
| | | | $OC_6H_{13}$ | | $C_2H_5$ | | H | | |
| 15 | (T) | $R_8=$ | $CH_3$ | $R_9=$ | $C_2H_5$ | | | | Blue |
| | | | $C_6H_{13}$ | | H | | | | |
| 16 | (W) | $R_8=$ | $CH_3$ | | | | | | Purple |
| | | | phenyl | | | | | | Purple |
| 17 | (Z) | $R_{11}=$ | $OC_2H_5$ | $R_{12}=$ | H | | | | Green-Blue |
| | | | $OC_6H_{13}$ | | H | | | | |

Preparation C

Preparation of 2-(2-chloro-4-diethylaminobenzoyl)-3-quinoxalinic acid.

In this preparation, m-chloro-N,N-diethylaniline (K, wherein $R_3=Cl$, $R_4=H$, $R_5=R_6=C_2H_5$ and $R_7=H$) is combined with 2,3-quinoxalinic anhydride (I, wherein $R_1=R_2=H$) to yield the title compound. This preparation can also be completed using 6,7-dibutyl-2,3-quinoxalinic anhydride (I, wherein $R_1=R_2=C_4H_9$) and 6,7-dibutoxy-2,3-quinoxalinic anhydride (I, wherein $R_1=R_2=OC_4H_9$). Two-tenths mole of the aniline (chloro-dimethylaniline can also be used) and 0.2 mole of anhydrous aluminum chloride are added to 250 milliliters of tetrachloroethane and stirred for about 10 minutes. To that system, initially cooled to about 5 centigrade. The mixture is then poured into ice and ammonia and extracted with toluene. The toluene is dried using sodium sulfate, concentrated, and chromatographed on alumina using chloroform followed by ethyl acetate as the eluting solvents. Solvent from the eluted fraction is evaporated and the material is recrystallized several times from chloroform-petroleum ether. The resulting product is 1,1-bis(3-chloro-4-diethylaminophenyl)-1-[H]-3-[H]-furo[3,4-b]quinoxalin-3-one, exhibits a melting point of 214°–216° centigrade, and a solution of the product imparts a green-yellow color to paper coated with silton clay and a green color to paper coated with a phenolic resin.

In an elemental analysis, the calculated elemental amounts for the above product, by weight percent, are:

C, 65.58; N, 10.20; H. 5.50; Cl, 12.90. The elemental amounts found in the above preparation were: C, 65.66; N, 10.21; H, 5.43; Cl, 13.01.

diethyl-m-phenetidine (K, wherein $R_3$=$OCH_3$, $R_4$=H, $R_5$=$R_6$=$C_2H_5$, $R_7$=H), and 7 milliliters of acetic anhydride is heated at about 55° centigrade for about 1½

TABLE III

| Ex. No. | Moiety | | Substituents | | | | | | Color |
|---|---|---|---|---|---|---|---|---|---|
| 19 | (K) | $R_3$= | H | $R_4$= | H | $R_5$=$R_6$= | $C_2H_5$ | $R_7$= H | Green-Blue |
| | | | H | | $OC_6H_{13}$ | | $C_2H_5$ | H | |
| | | | $OC_2H_5$ | | H | | $C_2H_5$ | H | Green-Blue |
| | | | $CH_3$ | | H | | $C_2H_5$ | H | Green |
| 20 | (L) | $R_8$= | $CH_3$ | $R_9$= | $CH_3$ | | | | Green |
| 21 | (M) | $R_8$= | $CH_3$ | $R_9$= | $C_2H_5$ | $R_{10}$= | H | | Green-blue |
| | | | $CH_3$ | | H | | $CH_3$ | | " |
| | | | $CH_3$ | | H | | $OCH_3$ | | " |
| 22 | (W) | $R_8$= | H | $R_9$= | $CH_3$ | | | | Green |
| | | | H | | phenyl | | | | Blue |

PREPARATION D

Preparation of 2(1ethyl-2-methylindol-3-yl)-3-quinoxalinic acid.

In this preparation, 1-ethyl-2-methylindole (M, wherein $R_8$=$CH_3$, $R_9$=$C_2H_5$ and $R_{10}$=H) is combined with 2,3-quinoxalinic anhydride (I, wherein $R_1$=$R_2$=H) to yield the title compound. This preparation can also be completed using 6,7-di-(dimethylamino)-2,3-quinoxalinic anhydride(I, wherein $R_1$=$R_2$=$N(CH_3)_2$) and 6-hexyl-2,3-quinoxalinic anhydride (I, wherein $R_1$=$C_6H_{13}$, $R_2$=H). A mixture of 0.02 mole of the quinoxalinic anhydride and 0.02 mole of the indole is heated on a steam bath for four hours. The hardened mass is cooled and extracted with an ammonia solution and the ammonia solution is washed with toluene. The so-washed ammonia solution is then acidified to precipitate this reaction product. The precipitate is filtered, dried and recrystallized several times from acetonitrile. The resulting product exhibits a melting point of 139°-140° centigrade.

In an elemental analysis, the calculated elemental amounts for the title compound, by weight percent, are: C, 70.18; N, 11.69; H, 4.77. The elemental amounts found in the above preparation were: C, 69.89; N, 11.58; H, 4.79.

EXAMPLE 23

Combining a quinoxalinic acid from Preparation D, above, with an indole, results in a compound of this invention. This example will be given with details of the reaction conditions and will be followed by a table of exemplary compounds. A mixture of 1.0 gram of the title compound from Preparation D, 0.6 gram of N,N-diethyl-m-phenetidine and 7 milliliters of acetic anhydride is heated at about 55° centigrade for about 1½ hours and is then added to ice and ammonia and extracted with toluene. The toluene is dried using sodium sulfate and then evaporated. The residue is recrystallized from acetonitrile and exhibits a melting point of 213.5°-214.4° centigrade. The resulting product is 1-(1-ethyl-2-methylindol-3-yl)-1-)2-ethoxy- 4-diethylaminophenyl)-1-[H]-3-[H]-furo[3,4-b]-quinoxalin-3-one and a solution of the product imparts a blue color to paper coated with a phenolic resin or silton clay or a combination of the two.

It can be pointed out that the product of this Example 23 is the same as the second product in previous Example 14, prepared by a different method.

TABLE IV

| Ex. No. | Moiety | | Substituents | | | | | | Color |
|---|---|---|---|---|---|---|---|---|---|
| 24 | (K) | $R_3$= | $CH_3$ | $R_4$= | H | $R_5$=$R_6$= | $C_2H_5$ | $R_7$= H | Green |
| 25 | (L) | $R_8$= | $CH_3$ | $R_9$= | $CH_3$ | | | | Red |
| | | | $CH_3$ | | phenyl | | | | Red |
| | | | $C_2H_5$ | | H | | | | |
| 26 | (M) | $R_8$= | $CH_3$ | $R_9$= | $C_2H_5$ | $R_{10}$= | H | | Purple |
| | | | $CH_3$ | | H | | $CH_3$ | | Red |
| | | | $CH_3$ | | H | | $C_6H_{13}$ | | |
| | | | $CH_3$ | | H | | $OCH_3$ | | Red |
| | | | $CH_3$ | | H | | $OC_6H_{13}$ | | |
| | | | phenyl | | | | $C_2H_5$ | H | Purple |
| 27 | (T) | $R_8$= | $CH_3$ | $R_9$= | $C_2H_5$ | | | | Purple |
| 28 | (W) | $R_9$= | $CH_3$ | | | | | | Red |

Preparation E

Preparation of 2(2-methoxy-4-diethylaminobenzoyl)-6,7-dimethyl-3-quinoxalinic acid.

In this preparation N,N-diethyl-M-toluidine (K, wherein $R_3$=$CH_3$, $R_4$=H, $R_5$=$R_6$=$C_2H_5$, $R_7$=H) is combined with 6,7-dimethyl-2,3-quinoxalinic anhydride (I, wherein $R_1$=$R_2$=$CH_3$) to yield the title compound. This preparation can also be completed using 6,7-dipropoxy-2,3-quinoxalinic anhydride (I, wherein $R_1$=$R_2$=$OC_3H_7$) and 6-hexyl-2,3-quinoxalinic anhydride (I, wherein $R_1$=$C_6H_{13}$, $R_2$=H). A mixture of 0.1 mole of the toluidine and 0.1 mole of anhydrous aluminum chloride is stirred in 100 milliliters of tetrachloroethane. The mixture is cooled to less than 10 degrees centigrade and 0.02 mole of the 2,3-quinoxalinic anhydride is slowly added. The mixture is stirred for about 2 hours and then poured into ice and concentrated hydrochloric acid and steam distilled. The distillate is made basic and filtered. The material filtered out is redissolved in dilute hydrochloric acid, the pH is adjusted to 3.5 and the system is filtered again. The material filtered out is dissolved in ammonia solution and the pH is adjusted to 3.0. The system is filtered again and the dried residue is title compound.

Example 29

Combining a quinoxalinic acid from Preparation E, above, with a toluidene, results in a compound of this invention. This example will be given with details of the reaction conditions and will be followed by a table of exemplary compounds. A mixture of 1.0 gram of the title compound from Preparation E, 0.45 grams of N,N-diethyl-m-toluidine (K, wherein $R_3=CH_3$, $R_4=H$, $R_5=R_6=C_2H_5$, $R_7=H$), and 10 milliliters of acetic anhydride are refluxed for about 1 hour and poured into ice and ammonia. The system is extracted twice with toluene, dried in the toluene using sodium sulfate, and the toluene is evaporated. The residue is dissolved in chloroform and chromatographed on alumina using chloroform as the eluting solvent. Solvent from the eluted fraction is evaporated and the material is recrystallized three times from toluene-petroleum ether and once from toluene. A solution of the resulting product imparts a green color to paper coated with a phenolic resin or silton clay or a combination of the two.

nolic resin. This example can also be completed using 1-methyl-2,5-dihexoxypyrrole.

EXAMPLE 37

A mixture of 0.6 grams of the quinoxalinic acid of Preparation F and 0.75 grams of 1-ethyl-2-methylindole (M, wherein $R_8=CH_3$, $R_9=C_2H_5$) is combined in a solution of acetic anhydride to yield 1,1-bis(1-ethyl-2-methylindol-3-yl)-6,7-dichloro-1-[H]-3-[H]-furo[3,4-b]quinoxalin-3-one which imparts purple color to paper coated with phenolic resin.

Preparation G

Preparation of 6.7-dimethyl-2,3-quinoxaline anhydride

Twenty-five grams of dihydroxytartaric acid is added to a boiling solution of 25 grams of 4,5-dimethyl-o-phenylene diamine in 500 milliliters of water. Hydrochloric acid gas is passed through the mixture. The mixture is cooled and solid product is separated by filtration. The separated material is dried, dissolved in 150 milliliters of acetic anhydride, and refluxed for about 15 minutes. The system is cooled and title compound having a decomposition point of 241° centigrade is separated by filtration. This preparation can also be completed using 4,5-dinitro-o-phenylene diamine and 4,5-dichloro-o-phenylene diamine.

TABLE V

| Ex. No. | Moiety | Substituents | | | | | | Color |
|---|---|---|---|---|---|---|---|---|
| 30 | (K) | $R_3=$ | $OC_2H_5$ | $R_4=$ | H | $R_5=R_6=$ | $C_2H_5$ | $R_7=H$ | Green |
| | | | Cl | | H | | $C_2H_5$ | H | Green |
| | | | $NO_2$ | | H | | $C_2H_5$ | H | Yellow |
| 31 | (L) | $R_8=$ | $CH_3$ | $R_9=$ | $CH_3$ | | | | Blue |
| | | | $CH_3$ | | phenyl | | | | Blue |
| 32 | (M) | $R_8=$ | $CH_3$ | $R_9=$ | $C_2H_5$ | $R_{10}=$ | H | | Blue-green |
| | | | phenyl | | $C_2H_5$ | | H | | Green |
| | | | $CH_3$ | | H | | $CH_3$ | | Green-blue |
| | | | $CH_3$ | | H | | $OCH_3$ | | Green-blue |
| 33 | (T) | $R_8=$ | $CH_3$ | $R_9=$ | $C_2H_5$ | | | | Blue |
| 34 | (W) | $R_9=$ | $CH_3$ phenyl | | | | | | Blue |
| 35 | (Z) | $R_{11}=$ | $OCH_3$ | $R_{12}=$ | H | | | | Purple |
| | | | $OCH_3$ | | $CH_3$ | | | | Purple |
| | | | $OCH_3$ | | $C_2H_5$ | | | | |

Prepartion F

Preparation of 6,7dichloro-2,3-quinoxalinic acid

The title compound is prepared by adding 18.5 grams od dihydroxy tartaric acid to a solution of 25.1 grams of 4,5-dichloro-0-phenylene diamine in 220 milliliters, each, of water and ethanol, stirring for about five minutes, acidifying with hydrochloric acid abd filtering off the reaction product.

EXAMPLE 36

As an example of preparing compounds of this invention by a method not above described, the quinoxalinic acid of Preparation F is combined with reactant moieties to yield bisquinoxaline compounds.

A mixture of 0.6 grams of the quinoxalinic acid and 0.6 grams of 1,2,5-trimethylpyrrole (L, wherein $R_8=R_9=CH_3$) is combined in a solution of acetic anhydride to yield 1,1-bis(1,2,5-trimethylpyrr-3-yl)-6,7-dichloro-1-[H]-3-[H]-furo[3,4-b]quinoxalin-3-one which imparts orange color to paper coated with phe-

EXAMPLE 38

Bis-quinoxaline compounds are prepared in the following examples.

A mixture of 0.6 grams of the quinoxaline anhydride of Preparation G and 0.9 grams of N,N-diethyl-m-toluidine (K, wherein $R_3=CH_3$, $R_4=H$, $R_5=R_6=C_2H_5$, $R_7=H$), in 10 milliliters of acetic anhydride are refluxed for about 1 hour, dilute ammonia is added, the mixture is extracted with toluene and the reaction product, 1,1-bis(2-methyl-4-diethylaminophenyl)-6,7-dimethyl-1-[H]-3-[H]-furo[3,4-b]quinoxalin-3-one, is isolated. The productimparts a green color to paper coated with a phenolic resin.

EXAMPLE 39

The procedure of Example 38 is repeated using 0.6 grams of the quinoxaline anhydride of Preparation G and 1.0 gram of N,N-diethyl-m-phenetidine (K, wherein $R_3=OCH_3$, $R_4=H$, $R_5=R_6=C_2H_5$, $R_7=H$). The reaction product is 1,1-bis(2-methoxy-4-diethylaminophenyl)-6,7-dimethyl-1-[H]-3-[H]-furo[3,4-b]quinoxalin-3-one and imparts a green-blue color to paper coated with a phenolic resin.

Other eligible compounds analogous to those of above Examples 38 and 39 include the following:

TABLE VI

| Ex. No. | Moiety | | Substituents | | | | | |
|---|---|---|---|---|---|---|---|---|
| 40 | (K) | $R_3=$ | $CH_3$ | $R_4=$ | H | $R_5=R_6=$ | $C_2H_5$ | $R_7=$ | $C_4H_9$ |
| | | | $CH_3$ | | H | | $C_2H_5$ | | $N(C_4H_9)_2$ |
| | | | $C_6H_{13}$ | | H | | $C_2H_5$ | | H |
| 41 | (K) | $R_3=$ | $OC_2H_5$ | $R_4=$ | H | $R_5=R_6=$ | $C_2H_5$ | $R_7=$ | $C_6H_{13}$ |
| | | | $OC_2H_5$ | | H | | $C_2H_5$ | | $OC_6H_{13}$ |

What is claimed is:

1. A chromogenic compound represented by the formula:

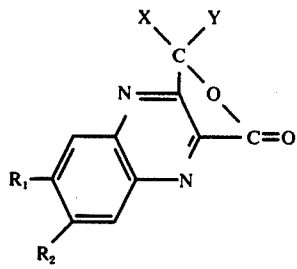

wherein X is one of K, L, M, T, W and Z and Y is one of K, L, M and T; and

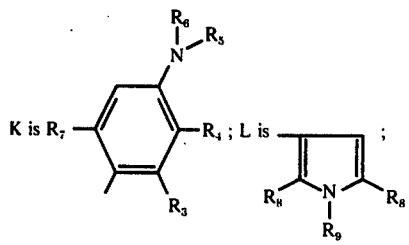

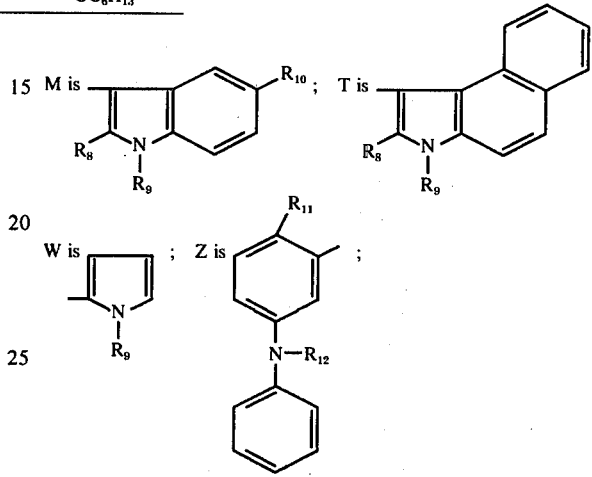

$R_1$, $R_2$, $R_3$, $R_4$ and $R_7$ are hydrogen, chlorine, nitro, alkyl, alkoxy, and dialkylamino, wherein alkyl and alkoxy are less than seven carbon atoms; $R_5$ and $R_6$ hydrogen, phenyl, benzyl, and alkyl, wherein alkyl is less than seven carbon atoms and, additionally, when one of $R_5$ and $R_6$ is phenyl, alkyl and alkoxy wherein alkyl and alkoxy are less than seven carbon atoms; $R_9$ is hydrogen, phenyl and alkyl wherein alkyl is less than seven carbon atoms; $R_{10}$ is hydrogen, alkyl and alkoxy wherein alkyl and alkoxy are less than seven carbon atoms; $R_{11}$ is alkoxy less than seven carbon atoms; $R_{12}$ is hydrogen, methyl and ethyl.

2. The chromogenic compound of claim 1 wherein Y is K.

3. The chromogenic compound of claim 2 wherein X is K.

4. The chromogenic compound of claim 1 wherein Y is M and X is one of L, M, T, W and Z.

5. The chromogenic compound of claim 4 wherein X is M.

6. The chromogenic compound of claim 1 wherein X and Y are L.

* * * * *

UNITED STATES PATENT AND TRADEMARK OFFICE
CERTIFICATE OF CORRECTION

PATENT NO. : 4,020,068
DATED : April 26, 1977
INVENTOR(S) : Sheldon Farber

It is certified that error appears in the above-identified patent and that said Letters Patent are hereby corrected as shown below:

Column 9, line 18, Ex. No. 22, cancel "$R_8$=H".

Column 9, line 19, Ex. No. 22, cancel "H".

Claim 1, column 14, line 33, after "$R_6$" insert ---are---.

Claim 1, column 14, line 36, after "phenyl" insert ---or benzyl, the other is hydrogen or methyl; $R_8$ is hydrogen, phenyl,---.

Signed and Sealed this

Twentieth Day of September 1977

[SEAL]

Attest:

RUTH C. MASON
*Attesting Officer*

LUTRELLE F. PARKER
*Acting Commissioner of Patents and Trademarks*